United States Patent
Herzig et al.

(10) Patent No.: US 7,964,751 B2
(45) Date of Patent: Jun. 21, 2011

(54) ENANTIOMERS OF AMINO-PHENYL-ACETIC ACID OCTADEC-9-(Z) ENYL ESTER, THEIR SALTS AND THEIR USES

(75) Inventors: Yaacov Herzig, Raanana (IL); Jeffrey Sterling, Jerusalem (IL); Vladimir Ioffe, Kfar Saba (IL); Yuriy Raizi, Natanya (IL); Istvan Miskolczi, Banat utca (HU); Andras Zekany, Tessedik Samuel (HU)

(73) Assignee: Yeda Research and Development Co. Ltd., Rehovot (IL)

( * ) Notice: Subject to any disclaimer, the term of this patent is extended or adjusted under 35 U.S.C. 154(b) by 58 days.

(21) Appl. No.: 12/072,405

(22) Filed: Feb. 25, 2008

(65) Prior Publication Data

US 2008/0221209 A1    Sep. 11, 2008

Related U.S. Application Data

(60) Provisional application No. 60/903,738, filed on Feb. 26, 2007.

(51) Int. Cl.
    C07C 69/02    (2006.01)
(52) U.S. Cl. ........................................................ 560/231
(58) Field of Classification Search ........................ None
    See application file for complete search history.

(56) References Cited

U.S. PATENT DOCUMENTS

| | | |
|---|---|---|
| 3,592,930 A | 7/1971 | Katz et al. |
| 4,152,423 A | 5/1979 | Adam et al. |
| 5,194,451 A | 3/1993 | Katz |
| 5,340,588 A | 8/1994 | Domb |
| 5,540,931 A | 7/1996 | Hewitt et al. |
| 5,807,820 A | 9/1998 | Elias |
| 5,817,629 A | 10/1998 | Warren et al. |
| 5,910,306 A | 6/1999 | Alving et al. |
| 5,968,524 A | 10/1999 | Watson et al. |
| 5,984,764 A | 11/1999 | Saito et al. |
| 6,114,337 A | 9/2000 | Pugliese et al. |
| 6,118,020 A | 9/2000 | Buyuktimkin et al. |
| 6,210,700 B1 | 4/2001 | Valente et al. |
| 6,280,755 B1 | 8/2001 | Berger et al. |
| 6,331,568 B1 | 12/2001 | Horrobin |
| 6,365,628 B1 | 4/2002 | Berge |
| 6,458,772 B1 | 10/2002 | Zhou et al. |
| 2004/0247604 A1 | 12/2004 | Cohen et al. |
| 2006/0173053 A1 | 8/2006 | Shinitzky et al. |
| 2006/0183797 A1 | 8/2006 | Cohen et al. |

FOREIGN PATENT DOCUMENTS

| | | |
|---|---|---|
| WO | WO 99/04632 | 2/1999 |
| WO | WO 01/00139 | 1/2001 |
| WO | WO 02/083058 | 10/2002 |
| WO | WO 02/083122 | 10/2002 |
| WO | WO 2004/032824 | 4/2004 |
| WO | WO 2004032824 A2 * | 4/2004 |

OTHER PUBLICATIONS

U.S. Appl. No. 12/072,304, Hayardeny-Nisimov.
International Search Report issued on Sep. 11, 2002 in connection with PCT Application No. PCT/IL02/00294, international filing date Apr. 11, 2002.
International Search Report issued on Feb. 20, 2003 in connection with PCT Application No. PCT/IL02/00295, international filing date Apr. 11, 2002.
International Search Report issued on Jul. 15, 2004 in connection with PCT/IL03/00820, international filing date Oct. 9, 2003.
International Search Report issued on Jun. 2, 2008 in connection with PCT/US08/02471, international filing date Feb. 25, 2008.
International Search Report issued on Jun. 18, 2008 in connection with PCT/US08/02472, international filing date Feb. 25, 2008.
Intl. Preliminary Examination Report issued on Jun. 24, 2003 in connection with PCT Appl. No. PCT/IL02/00294, intl. filing date Apr. 11, 2002.
Intl. Preliminary Examination Report issued on Feb. 19, 2004 in connection with PCT Appl. No. PCT/IL02/00295, international filing date Apr. 11, 2002.
European Search Report issued on Jul. 1, 2004 in connection with European Patent Application No. 02761953.5.
European Search Report issued on Nov. 11, 2004 in connection with European Patent Application No. 02724588.5.
Sands, J. (1979) "Extreme Sensitivity of Enveloped Viruses . . . to Monoglycerides and Alcohols" Antimicrobial Agents and Chemotherapy 15(1):67-73.
Snipes, W. (1977) "Inactivation of Lipid-Containing Viruses by Long-Chain Alcohols" Antimicrobial Agents and Chemotherapy 11(1):98-104.
Notification Concerning Transmittal of International Preliminary Report on Patentability issued Sep. 3, 2009 in connection with PCT International Application No. PCT/US2008/002472.
International Preliminary Report on Patentability issued Aug. 26, 2009 in connection with PCT International Application No. PCT/US2008/002472.

* cited by examiner

*Primary Examiner* — Sudhakar Katakam
(74) *Attorney, Agent, or Firm* — John P. White; Cooper & Dunham LLP

(57) ABSTRACT

Disclosed are enantiomers of amino-phenyl-acetic acid octadec-9-(Z)-enyl ester, and salts thereof, including pharmaceutical compositions, uses and a process for the manufacture thereof.

10 Claims, No Drawings

ENANTIOMERS OF
AMINO-PHENYL-ACETIC ACID
OCTADEC-9-(Z) ENYL ESTER, THEIR SALTS
AND THEIR USES

The application claims benefit of U.S. Provisional Application No. 60/903,738, filed Feb. 26, 2007, the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

Inflammation is commonly divided into three phases: acute inflammation, the immune response and chronic inflammation. Acute inflammation is the initial response to tissue injury and is mediated by the release of histamine, serotonin, bradykinin, prostaglandins and leukotrienes. The immune response, usually preceded by the acute inflammation phase, occurs when immunologically competent cells are activated in response to foreign organisms or antigenic substances liberated during the acute or chronic inflammatory response. The outcome of the immune response for the host may be beneficial, as it causes invading organisms to be phagocytosed or neutralized. However, the outcome may be deleterious if it leads to chronic inflammation without resolution of the underlying injurious process, as occurs in rheumatoid arthritis.

Inflammation treatments slow or arrest the tissue-damaging process as well as relieve pain, which is the presenting symptom and the major continuing complaint of the patient.

Anti-inflammatory agents are usually classified as steroidal or glucocorticoids and nonsteroidal anti-inflammatory agents (NSAIDs). The glucocorticoids are powerful anti-inflammatory agents but the high toxicity associated with chronic corticosteroid therapy generally limits their use except to certain acute inflammatory conditions. Therefore, the nonsteroidal anti-inflammatory drugs have assumed a major role in the treatment of chronic conditions such as rheumatoid arthritis.

Among the non-steroidal anti-inflammatory agents are included derivatives of aminoarylcarboxylic acids, arylacetic acids, arylbutyric acids, arylcarboxylic acids, arylpropionic acids, pyrazole, pyrazolone, salicylic acid and some other derivatives of different chemical structure, including specific anti-arthritic/anti-rheumatic agents.

Racemic amino-phenyl-acetic acid octadec-9-(Z)enyl ester has been described (WO 2004/032824 A2); however, enantioselective preparation of the compound has thus far, not been taught. It would be highly desirable to provide these compounds enantioselectively and further provide succinct methods for their preparation. Several obstacles have prevented these compounds from being prepared enantioselectively.

SUMMARY OF THE INVENTION

This invention provides an enantiomerically pure or enantiomerically enriched compound selected from the group consisting of (R)-amino-phenyl-acetic acid octadec-9-(Z)-enyl ester, (S)-amino-phenyl-acetic acid octadec-9-(Z)-enyl ester, and a pharmaceutically acceptable salt thereof.

The invention also provides a method of determining the enantiomeric purity of a composition comprising amino-phenyl-acetic acid octadec-9-(Z)-enyl ester or a steroisomer of amino-phenyl-acetic acid octadec-9-(Z)-enyl ester comprising: analyzing the composition using chiral chromatography under suitable conditions; analyzing an enantiomerically pure stereoisomer of amino-phenyl-acetic acid octadec-9-(Z)-enyl ester using chiral chromatography under the same conditions as in step a; and comparing the chromatographic analyses of step a and step b, thereby determining the enantiomeric purity of the composition.

DETAILED DESCRIPTION OF THE INVENTION

This invention provides an enantiomerically pure or enantiomerically enriched compound selected from the group consisting of (R)-amino-phenyl-acetic acid octadec-9-(Z)-enyl ester, (S)-amino-phenyl-acetic acid octadec-9-(Z)-enyl ester, and a pharmaceutically acceptable salt thereof.

In an embodiment, the invention provides a compound which is enantiopure.

In another embodiment of the invention the compound is (R)-amino-phenyl-acetic acid octadec-9-(Z)-enyl ester or a pharmaceutically acceptable salt thereof.

In another embodiment of the invention the compound is (S)-amino-phenyl-acetic acid octadec-9-(Z)-enyl ester or a pharmaceutically acceptable salt thereof.

In another embodiment of the invention, the compound is in the form of a pharmaceutically acceptable salt.

Another embodiment of the invention provides a pharmaceutical composition comprising the compound and at least one pharmaceutically acceptable carrier.

An embodiment of the invention also provides a method of manufacturing a compound comprising: heating a mixture of oleyl alcohol and a stereoisomer of phenylglycine chloride hydrochloride in a polar aprotic solvent; and isolating the compound from the mixture.

In an embodiment of the invention the method the polar aprotic solvent is acetonitrile, DMSO, dimethylformamide, hexamethyl phosphorotriamide, toluene or ethyl acetate.

In yet another embodiment of the method the solvent in step a) is acetonitrile.

In another embodiment the invention provides a method of treatment of a subject suffering from psoriasis, alopecia areata, pemphigus vulgaris, contact dermatitis, atopic dermatitis, allergies, vitiligo or inflammatory skin disorders comprising administering to the subject a therapeutically effective amount of the compound of the invention or of the pharmaceutical composition.

In yet another embodiment, the invention provides a method of treatment of a subject suffering from an inflammatory disease comprising administering to the subject a therapeutically effective amount the compound of the invention or of the pharmaceutical composition.

In yet another embodiment of the method the disease is psoriasis.

In yet another embodiment of the method the disease is atopic dermatitis.

In yet another embodiment of the method the disease is contact dermatitis.

The invention also provides a method of determining the enantiomeric purity of a composition comprising amino-phenyl-acetic acid octadec-9-(Z)-enyl ester or a steroisomer of amino-phenyl-acetic acid octadec-9-(Z)-enyl ester comprising: analyzing the composition using chiral chromatography under suitable conditions; analyzing an enantiomerically pure stereoisomer of amino-phenyl-acetic acid octadec-9-

(Z)-enyl ester using chiral chromatography under the same conditions as in step a; and comparing the chromatographic analyses of step a and step b, thereby determining the enantiomeric purity of the composition.

PCT International Application Publication No. WO 2004/032824 discloses racemic aminophenylacetic acid octadec-(Z)-9-enyl ester HCl (compound 11). The enantiomers of this compound were not disclosed in WO 2004/032824.

The desired use of the compounds described herein is as a medicament to prevent inflammation. The hurdles to obtain governmental regulatory approval, e.g. FDA approval, are much greater for racemic compounds than for enantiopure compounds. For example, the FDA (U.S. Food and Drug Administration) has put forth a policy on the development of new stereoisomeric drugs stating that if the drug product is a racemate, then the pharmacokinetic profile of each enantiomer and of the racemate needs to be investigated. Manufacturers are required to monitor the enantiomers individually to determine such properties as dose linearity and the effects of altered metabolic or excretory function and drug-drug interactions. In short, if a drug is a racemic mixture, the FDA requires testing of the racemate and both enantiomers individually to understand their effects. Thus, there is an incentive to prepare the desired compound enantioselectively, and not as a racemic mixture.

Enantioselective preparation of esters of phenylglycine is a challenging endeavor. (Clark et al., 1976, *Journal of the Chemical Society: Perkin Transactions* 1, 5:471-474) Amino acids can tautomerize and interconvert between their keto and enol tautomers; however in acidic or aqueous media, most will prefer the keto tautomer, making resolution of enantiomers possible. As most commonly encountered, tautomerization results in the formal migration of a hydrogen atom or proton, accompanied by a switch of a single bond and adjacent double bond. In solutions where tautomerization is possible, a chemical equilibrium of the tautomers will be reached. The exact ratio of the tautomers depends on several factors, including temperature, solvent, and pH. (see Organic Chemistry, McMurry, 2003) In the case of phenylglycine however, the phenyl ring stabilizes the enol form through double bond conjugation, giving rise to an equilibrium of both tautomers. Formation of the enol tautomer, and thus formation of an olefinic bond removes the previous chirality of the amino acid, and results in racemization of products. The stabilization of this achiral enol tautomer, makes enantioselective preparation of phenylglycine derivatives difficult; enantioselective preparation of amino-phenyl-acetic acid octadec-9-(Z)-enyl ester has not been reported prior to this invention.

In addition to their use as therapeutic agents, the enantioenriched compounds of the invention can be used as analytical markers, useful for determining the amount of each enantiomer in a mixture of the two enantiomers. Such an analysis may be performed using chiral chromatography.

This invention also provides stable enantiopure or stable enantioenriched (R)-amino-phenyl-acetic acid octadec-9-(Z)-enyl ester HCl or (S)-amino-phenyl-acetic acid octadec-9-(Z)-enyl ester HCl, and a method for maintaining stability and preventing racemization. As used herein, a composition is "stable" if no more than 6.0% racemizes after 21 hours, preferably no more than 0.3% racemizes after 21 hours. A composition is also considered stable if after 3 hours no more than 3.3% racemizes, preferably no more than 1.5%, more preferably no more than 0.4%, yet more preferably no more than 0.3% racemizes.

Within the context of the invention, the term "isolated" means absent of another compound, in particular, absent of another enantiomer, as determined by standard currently available methods of analysis.

"Enantioenriched compound" or "enantiomerically enriched compound" as used here means a composition of a chiral substance whose enantiomeric ratio is greater than 50:50 but less than 100:0 of the specified enantiomer. (See IUPAC Compendium of Chemical Terminology, "Goldbook", Second Edition, 1997).

"Enantiopure compound" or "enantiomerically pure compound" as used herein means a composition containing molecules all having the same chirality sense (within the limits of detection). (See IUPAC Compendium of Chemical Terminology, "Goldbook", Second Edition, 1997).

"Racemic mixture", "racemic compound", "racemic composition", "racemic", "racemate" and "(±)" terminology are used interchangeably herein.

Certain embodiments of the disclosed compounds can contain a basic functional group, such as amino or alkylamino, and are thus capable of forming pharmaceutically acceptable salts with pharmaceutically acceptable acids, or contain an acidic functional group and are thus capable of forming pharmaceutically acceptable salts with bases. The instant compounds may be in a salt form. As used herein, a "salt" is salt of the instant compounds which has been modified by making acid or base salts of the compounds. In the case of compounds used for treatment of inflammation, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, the term "effective amount" refers to the quantity of a component that is sufficient to yield a desired therapeutic response without undue adverse side effects (such as toxicity, irritation, or allergic response) commensurate with a reasonable benefit/risk ratio when used in the manner of this invention. For example, an amount effective to inhibit or reverse inflammation, or for example to inhibit, attenuate or reverse symptoms of inflammation. The specific effective amount will vary with such factors as the particular condition being treated, the physical condition of the patient, the type of mammal being treated, the duration of the treatment, the nature of concurrent therapy (if any), and the specific formulations employed and the structure of the compounds or its derivatives.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutical carrier.

The compounds can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone but are generally mixed with a pharmaceutically acceptable carrier. This carrier can be a solid or liquid, and the type of carrier is generally chosen based on the type of administration being used. In one embodiment the carrier can be a monoclonal antibody. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.).

The instant compounds may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

The esters of the present invention are in general crystalline, non-hygroscopic and water-soluble and are more easily purified and formulated for oral and parenteral formulation than the starting saturated or cis-unsaturated alcohols.

Inflammatory diseases, disorders, or conditions that can be treated with the immunomodulators of the present invention include, but are not limited to, immunoloically-mediated chronic or acute inflammatory diseases, psoriasis, alopecia areata, pemphigus vulgaris, contact dermatitis, atopic dermatitis, allergies, vitiligo or inflammatory skin disorders.

EXPERIMENTAL DETAILS

The compounds of the invention were prepared by reacting the pure alcohol with optically pure 2-phenylglycine chloride hydrochloride (either commercially available or prepared by reacting phenylglycine with chlorinating agents, such as $PCl_5$ or a mixture of $PCl_5$ and $POCl_3$) in an appropriate solvent, preferably acetonitrile, at temperatures ranging from ambient to reflux, preferably reflux. Racemization was minimized under such conditions and no racemization occurred in the chiral center of the phenylglycine moiety under the preferred experimental conditions.

Example 1

(S)-Amino-phenyl-acetic acid octadec-9-(Z)-enyl ester HCl (Compound 1)

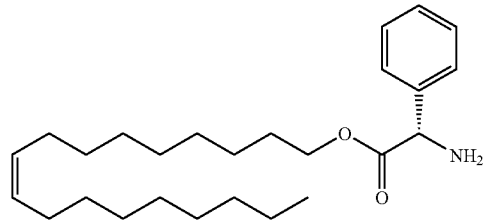

Oleyl alcohol (13.4 g, 99.7% purity) was added to a stirred mixture of L-phenylglycine chloride hydrochloride (10.3 g, Aldrich 344273, 97%) and acetonitrile (140 ml). The reaction mixture was refluxed for 3 hr, cooled to 2-4° C. and kept at this temperature for 2 hr under atmospheric conditions. The precipitated white solid was collected by filtration and crystallized from 9:1 acetone:ethanol mixture, and dried (in air at 20-25° C. or in a vacuum oven at 40° C.) to give 8.1 g (37%), mp 83.9-84.5° C., 100% enantiomeric excess (ee) determined by chiral HPLC before crystallization. The product was stored at ambient temperature in tightly closed vessels.

$^1$H and $^{13}$C NMR (600 MHz and 150 MHz, respectively, in CDCl$_3$) data are given in Table 1.

Example 2

(R)-Amino-phenyl-acetic acid octadec-9-(Z)-enyl ester HCl (Compound 2)

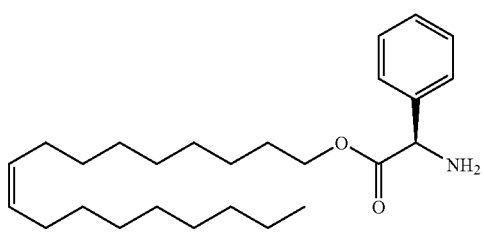

Oleyl alcohol (2.68 g, 99.7% purity) was added to a stirred mixture of D-phenylglycine chloride hydrochloride (2.06 g, Aldrich 344273 97% purity) and acetonitrile (60 ml). The reaction mixture was refluxed for ½ hr, cooled to 2-4° C. and kept at this temperature for 1 hr under atmospheric conditions. The precipitated white solid was collected by filtration and crystallized from acetone, and dried (in air at 20-25° C. or in a vacuum oven at 40° C.) to give 1.9 g (43%), mp 85.5-86.5° C., 100% ee as determined by chiral HPLC before crystallization. The product was stored at ambient temperature in tightly closed vessels. $^1$H and $^{13}$C NMR (600 MHz and 150 MHz, respectively, in CDCl$_3$) data are given in Table 1.

TABLE 1

$^1$H and $^{13}$C Chemical shifts of compounds 1 and 2 alcohol Esters

| position | Compounds 1 and 2 | |
|---|---|---|
| | $^1$H | $^{13}$C |
| 1' | — | 168.32 |
| 2' | 5.20$^d$ | 57.02 |
| NH$_3^+$ | 9.15$^e$ | — |
| 3' | — | 131.71 |
| 4' | 7.56 | 128.66 |
| 5' | 7.32 | 129.00 |
| 6' | 7.32 | 129.43 |
| 1 | 4.07, 3.99 | 66.64 |
| 2 | 1.48, 1.47 | 28.17 |
| 3 | 1.09 | 25.53 |
| 4 | 1.15 | a |
| 5 | 1.15 | a |
| 6 | 1.21 | a |
| 7 | 1.28 | 29.77$^b$ |
| 8 | 1.99 | 27.22$^c$ |
| 9 | 5.33 | 129.96 |
| 10 | 5.35 | 129.76 |
| 11 | 2.01 | 27.23$^c$ |
| 12 | 1.33 | 29.78$^b$ |
| 13 | 1.28 ± 0.03 | a |
| 14 | 1.28 ± 0.03 | a |
| 15 | 1.28 ± 0.03 | a |
| 16 | 1.28 ± 0.03 | 31.92 |
| 17 | 1.28 ± 0.03 | 22.69 |
| 18 | 0.88 | 14.12 | a 29.07, 29.21, 29.33, 29.33, 29.40, 29.54
$^{b,c}$values with the same superscript in the same column may be interchanged.
$^d$q, 7 Hz.
$^e$d, 7 Hz.

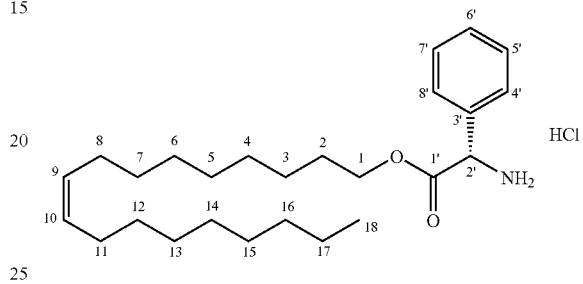

Example 3

Racemization in Various Solvents

A sample of (R)-Amino-phenyl-acetic acid octadec-9-(Z)-enyl ester HCl (Compound 2) was suspended in various solvents (2 mg/ml). The compound was 99.7% enantiomerically pure as determined by chiral HPLC. The presence of the S-isomer (compound 1) was measured after various time points. The amount of racemization in terms of percent (relative to compound 1+compound 2) is detailed in Table 2 below.

TABLE 2

Percent racemization (relative to compound 1 + compound 2) in aqueous solvents

| Time (hours) | Purified water | 0.1 N HCl | 0.9% NaCl solution | PBS, pH 7.4 |
|---|---|---|---|---|
| 0 | 0.4 | 0.4 | 0.9 | 0.4 |
| 1 | 3.8 | 0.4 | 1.2 | 7.2 |
| 2 | 7.2 | 0.4 | 2.3 | 12.3 |
| 3 | 10.3 | 0.3 | 3.3 | 15.0 |
| 4 | 13.9 | 0.3 | 3.0 | 17.9 |
| 21 | 38.2 | 0.3 | 6.0 | 47.0 |

Compound 2 undergoes racemization in various aqueous solvents.

Additionally, a sample of (R)-Amino-phenyl-acetic acid octadec-9-(Z)-enyl ester HCl (Compound 2) was suspended (2 mg/ml) in various acetate buffers and pure acetic acid in the pH range between 2.8 and 5.5, to evaluate enantiomeric stability at pH levels around the pKa of the compound (pKa=4.2).

The presence of the S-isomer (Compound 1) was measured by chiral HPLC after various time points. The amount in terms of percent (relative to compound 1+compound 2) is detailed in the table below.

TABLE 3

| Time, hr | 1% Acetic acid, pH 2.8 | Acetate Buffer, pH 3.5 | Acetate Buffer, pH 4.0 | Acetate Buffer, pH 5.0 | Acetate Buffer, pH 5.5 |
|---|---|---|---|---|---|
| 0 | 0.7 | 0.3 | 0.2 | 0.2 | 0.2 |
| 1 | 2.0 | 3.3 | 7.7 | 6.3 | 4.7 |
| 2 | 3.6 | 6.2 | 15.2 | 14.6 | 8.2 |
| 3 | 5.2 | 9.3 | 22.1 | 19.0 | 12.4 |
| 4 | 6.6 | 12.1 | 27.2 | 25.3 | 16.4 |

Example 4

Synthesis of aminophenylacetic acid octadec-(Z)-9-enyl ester HCl

To a solution of N-Boc L-phenylglycine (2.51 g, 10 mmol) in acetonitrile (50 ml), was added portionwise 1,1'-carbonyl-diimidazole (3.24 g, 20 mmol). The solution was stirred at room temperature for 1 h, oleyl alcohol (3.15 ml, 2.68 g, 10 mmol) was added, and the reaction mixture further stirred for 2 h at room temperature. The solvent was evaporated, the residue was dissolved in ethyl acetate (150 ml), washed successively with 5% $NaHCO_3$, 5% citric acid and water, dried on $MgSO_4$ and evaporated to dryness. The residue was dissolved in 1% HCl in ethyl acetate (100 ml), and the solution set aside for 6 h at room temperature, and evaporated to dryness. The residue thus obtained was crystallized from ether/n-hexane to give 1.6 g 3.65 mmol, 36.5% yield) of an off-white solid, mp 101-103° C. Racemic mixture was attained.

Elemental Analysis Calculated: C, 71.28; H, 10.12; N, 3.10. Found: C, 70.87; H, 10.33; N, 3.47.

H-NMR (200 MHz, DMSO-d6) (ppm) b: 0.85 (t, 3H, Me), 1.20-1.50 (m, 22H, 11CH2), 1.70-1.80 (m, 2H, CH2), 1.96 (ted, 4H, 2CH2), 4.15 (m, 2H, COOCH2), 5.25 (s, 1H, PhCHNH2), 5.27-5.39 (m, 2H, CH=CH), 7.40-7.60 (m, 5H, 30 Ph), 9.20 (br s, 3H, N+H3).

Discussion

This example is essentially the same as the Example 11 disclosed in WO 2004/032824; however, a single enantiomer, was used as a starting material. Nevertheless, the outcome was the same.

Example 5

Pharmacology

Delayed type hypersensitivity (DTH), a localized inflammatory reaction induced by cytokines secreted by certain TH cells when they encounter certain types of antigens, is an established experimental model for skin inflammation.

DTH reactions were induced in the abdomen skin of 8 week old female Balb/c mice, weighing 20 g each.

The mice were sensitized first by topical application of 100 µl of a 5% Oxazolone (4-Ethoxymethylene-2-phenyl-2-oxazolin-5-one; Sigma) solution in ethanol/acetone (3:1, vol/vol) to a shaved abdomen. The mice were anesthetized with I.P. injection of 0.2 ml/mouse of a stock solution prepared from Ketamine (1 ml)+Xylazine (1 ml)+Saline (8 ml). The anesthesia was done for the shaving of the abdomen and the first sensitization.

After 4 days the mice were challenged for the second time using 1% Oxazolone (4-Ethoxymethylene-2-phenyl-2-oxazolin-5-one; Sigma) solution in ethanol/acetone (3:1, vol/vol). The solution was pipetted onto the shaved abdomen of the mice.

Six days after the first sensitization, the right ear of each mouse was challenged with topical application of 20 µl (10 µl at each surface of the ear) of a 1% Oxazolone solution in olive oil/acetone (3:1, vol/vol).

Treatment was given 30 min after the elicitation by applying 40 µl (20 µl at each surface of the ear) of treatment compounds, as described before, on the challenged ear of each mouse.

After 24 hours, the extent of inflammation was measured using the mouse ear swelling test (caliper) and the percent inhibition induced by the treatment was quantified.

The experiment includes a positive control group which was administered Dexamethasone 2 mg/mouse, one untreated group as a negative control and one naïve group.

Baseline measurements of the ear were conducted before the first sensitization.

TABLE 4

| Compound | treatment mg/ml | Dose mg/mouse | Difference mm | % Inflamation[1] | % Inhibition[2] |
|---|---|---|---|---|---|
| | Negative control | | 0.29 | 115.45 | 0.00 |
| Racemic | 5 mg/ml | 0.2 | 0.18 | 69.43 | 38.46 |
| | 8 mg/ml | 0.32 | 0.17 | 73.53 | 39.98 |
| | 12.5 mg/ml | 0.5 | 0.11 | 43.08 | 60.14 |
| | 25 mg/ml | 1 | 0.04 | 13.68 | 87.76 |
| Compd 2 | 5 mg/ml | 0.2 | 0.17 | 71.13 | 39.39 |
| | 8 mg/ml | 0.32 | 0.11 | 41.68 | 62.12 |
| | 12.5 mg/ml | 0.5 | 0.13 | 50.31 | 55.71 |
| | 25 mg/ml | 1 | 0.09 | 35.01 | 68.53 |
| Compd 1 | 5 mg/ml | 0.2 | 0.23 | 87.18 | 20.75 |
| | 8 mg/ml | 0.32 | 0.09 | 34.76 | 68.53 |
| | 12.5 mg/ml | 0.5 | 0.06 | 25.84 | 77.86 |
| | 25 mg/ml | 1 | 0.05 | 17.70 | 83.68 |
| | Positive control[3] | 2 | 0.06 | 22.62 | 80.42 |
| | Naïve[4] | | 0.01 | 4.21 | 96.50 |

[1]Diff/Base line * 100
[2]1 − (Diff/Diff Vehicle) * 100
[3]Positive control was dexamethasone (50 mg/ml)
[4]Untreated animals Discussion Compounds 1, 2 and the racemic mixture, provide inhibition of inflammation in the above model.

What is claimed is:

1. A compound selected from the group consisting of (R)-amino-phenyl-acetic acid octadec-9-(Z)-enyl ester, (S)-amino-phenyl-acetic acid octadec-9-(Z)-enyl ester, and a pharmaceutically acceptable salt thereof, wherein the compound is an enantiopure compound; or wherein the compound is an enantiomerically enriched compound whose enantiomeric ratio of the specified enantiomer is greater than 50:50 but less than 100:0.

2. The compound of claim 1 which is enantiopure.

3. The compound of claim 1, which is (R)-amino-phenyl-acetic acid octadec-9-(Z)-enyl ester or a pharmaceutically acceptable salt thereof.

4. The compound of claim 1, which is (S)-amino-phenyl-acetic acid octadec-9-(Z)-enyl ester or a pharmaceutically acceptable salt thereof.

5. The compound of claim 1, in the form of a pharmaceutically acceptable salt.

6. A pharmaceutical composition comprising the compound of claim 1 and at least one pharmaceutically acceptable carrier.

7. A method of manufacturing a compound of claim 2 comprising:
   a) heating a mixture of oleyl alcohol and a stereoisomer of phenylglycine chloride hydrochloride in a acetonitrile; and
   b) isolating the compound from the mixture.

8. The pharmaceutical composition of claim 6, comprising enantiopure (R)-amino-phenyl-acetic acid octadec-9-(Z)-enyl ester or a pharmaceutically acceptable salt thereof, or enantiopure (S)-amino-phenyl-acetic acid octadec-9-(Z)-enyl ester or a pharmaceutically acceptable salt thereof.

9. The compound of claim 3 which is enantiopure.

10. The compound of claim 4 which is enantiopure.

* * * * *